(12) United States Patent
Hentrich et al.

(10) Patent No.: US 8,366,597 B2
(45) Date of Patent: Feb. 5, 2013

(54) DEVICE AND SYSTEM FOR ASSEMBLING CHAIN COMPONENTS TO A CHAIN CONTAINING RADIATION SOURCES

(75) Inventors: Axel Hentrich, Berlin (DE); Christoph Lederer, Berlin (DE)

(73) Assignee: Eckert & Ziegler Bebig GmbH, Berlin (DE)

(*) Notice: Subject to any disclaimer, the term of this patent is extended or adjusted under 35 U.S.C. 154(b) by 176 days.

(21) Appl. No.: 13/025,669

(22) Filed: Feb. 11, 2011

(65) Prior Publication Data
US 2011/0197565 A1    Aug. 18, 2011

(30) Foreign Application Priority Data
Feb. 12, 2010  (EP) .................................. 10153447

(51) Int. Cl.
*A61M 36/00*   (2006.01)
*A61M 36/04*   (2006.01)
(52) U.S. Cl. .................................... 600/7; 600/3; 600/8
(58) Field of Classification Search ............... 600/1–8, 600/407, 427, 431, 434
See application file for complete search history.

(56) References Cited

U.S. PATENT DOCUMENTS

| 4,815,449 | A  | * | 3/1989  | Horowitz ........................... 600/7 |
| 6,358,195 | B1 |   | 3/2002  | Green et al. |
| 6,454,696 | B1 |   | 9/2002  | Kindlein et al. |
| 6,837,844 | B1 | * | 1/2005  | Ellard et al. ....................... 600/7 |
| 7,022,062 | B1 | * | 4/2006  | Murphy ............................ 600/7 |
| 7,025,717 | B2 |   | 4/2006  | Tarone et al. |
| 7,041,048 | B2 | * | 5/2006  | Drobnik et al. .................... 600/7 |
| 7,066,872 | B2 | * | 6/2006  | Waksman et al. ................. 600/3 |
| 7,201,715 | B2 | * | 4/2007  | Burdette et al. .................. 600/3 |
| 7,229,401 | B2 | * | 6/2007  | Kindlein ........................... 600/7 |
| 8,066,627 | B2 | * | 11/2011 | Terwilliger et al. ............... 600/8 |
| 2008/0161635 | A1 |  | 7/2008  | Watson et al. |

FOREIGN PATENT DOCUMENTS

| EP | 1 070 519 A1 | 1/2001 |
| WO | WO 2005/002670 A1 | 1/2005 |
| WO | WO 2009/005528 A1 | 1/2009 |

OTHER PUBLICATIONS

European Search Report issued for European Patent Application No. 10153447.7 mailed on Jun. 14, 2010.

* cited by examiner

*Primary Examiner* — David B Jones
(74) *Attorney, Agent, or Firm* — Pearl Cohen Zedek Latzer, LLP

(57) ABSTRACT

A device is proposed for assembling chain components to a chain, wherein at least two chain components include radioactive radiation sources. The device includes a housing, a working channel which extends along a first axis of the housing, a loading unit connected to the working channel and having at least two receiving devices for chain component magazines, wherein at least one receiving device is configured to receive a radiation source magazine, as well as at least one means for ejecting the chain components received from the magazines, and an joining unit for joining chain components. The at least two receiving devices are positioned so that the magazines for chain components received therein are spaced along the first axis and positioned vertically above the working channel.

15 Claims, 19 Drawing Sheets

19  18

19  18

DEVICE AND SYSTEM FOR ASSEMBLING CHAIN COMPONENTS TO A CHAIN CONTAINING RADIATION SOURCES

CROSS-REFERENCE TO RELATED APPLICATION

This application claims priority from European Patent Application No. 10153447.7, filed Feb. 12, 2010, which is hereby incorporated by reference in its entirety.

FIELD OF INVENTION

The invention relates to a device and system for assembling chain components to a chain that contains radiation sources. Use of the device is intended for the manufacture of chains made from radiation sources and spacers for treatment of prostate cancer.

BACKGROUND OF THE INVENTION

It is known to implant in cancer patients, particularly prostate cancer patients, chains made from radiation sources or so-called seeds. To this end, single radiation sources are used as well as pre-configured seed chains constructed, for example, by alternating a radiation source and a non-active spacer. Implanting single radiation sources allows the single radiation sources to be positioned individually using suitable means. The inflammatory enlargement of the prostate after implantation, followed by swelling, can cause the radiation sources to migrate or shift its position. A radioactive chain prevents this shift in position because it connects the individual implants to each other.

New medical tests show that adherence to a radiation treatment individually tailored to the patient achieves the best results when treating tumors. To do this, the position of the individual radiation sources must be exactly adjusted to each patient.

WO 2009/005528 A1 discloses a device for joining freely configurable seed-spacer chains from five different magazines with adjacent implants. The chains are joined by telescoping the individual implants into one another. The magazines are selected by moving a slider transversely to the working channel. This slider is used to receive the individual magazines. Such selection by using a slider is very complex, however, because the slider with the magazines as well as the working channel for receiving the selected chain components must always be re-aligned. This can easily lead to components jamming in the device. Furthermore, since the magazines are made of transparent polymer, they are only radiation-proof in their packaging or after insertion into the loading device. For this reason, the magazine content is limited to about 20 radiation sources.

U.S. Pat. No. 7,025,717 B2 describes a device, which has two magazines with two adjacent implants, which allows a freely configurable assembly of radiation sources and spacers. The implants are, however, not connected to fixed chains.

U.S. Pat. No. 6,454,696 B1 describes round magazines arranged successively, in which the radiation sources and spacers are arranged concentrically about the magazine pivot point. The arrangement is disadvantageous, however, in that, due to this invention's design, the individual implants from the rear magazine must be pushed through the front magazine. Pushing through the various magazines can, however, cause the device to jam, which must be then corrected manually. Pushing chain components through various magazines is also known from U.S. Pat. No. 6,358,195 B1.

SUMMARY OF THE INVENTION

It is therefore an object of the invention to provide a device and system for joining radiation source chains, which gives the attending surgical staff the opportunity to implant the seed in a user-friendly way while adhering to an individual radiation treatment. User-friendly is to be understood here as related to the device operation and optimal radiation protection for the user. Accordingly, a device is proposed for assembling chain components to a chain, wherein at least one chain component consists of at least one radiation source. The device includes a housing and working channel that extends along a first axis of the housing. The device also includes a loading unit connected with the working channel and having at least two receiving devices for chain component magazines, whereby at least one receiving device is configured to receive a radiation source magazine, and has at least one means for ejecting the chain components from the received magazine. The device also includes an assembly device for joining the chain components. The at least two receiving devices are positioned so that magazines for chain components received therein are spaced along the first axis and provided vertically above the working channel. In other words, the receiving devices themselves are spaced along the first axis and provided vertically above the working channel.

The described invention should enable users to combine and join radiation sources and spacers (hereinafter collectively designated as implants) as chain segments in an almost unlimited configuration by using provided radiation source magazines and/or spacer magazines. Thus, the limitation known from the prior art can be avoided to a great extent. Operation of the device is simple and intuitive. The described device has a central working channel, in which the implants are deposited from above from the magazines. Depositing the implants from above into the central working channel allows the magazines to be aligned along the device's longitudinal axis. Thus, implants from the rear magazine do not have to be pushed through the front magazine, which could lead to jamming. This arrangement of the magazines prevents the magazine receiver from being additionally shifted vertically or at another angle to the longitudinal axis during magazine selection. In addition, by only using two magazines it is more difficult to confuse the magazines when releasing the implants.

The ejection mechanism is preferably a lever mechanism which allows a magazine's ejection lever to return to its starting position after implant release, but only allows redeployment once the previously released implant has been removed.

Preferably, the second receiving center is configured to accept a spacer magazine with spacers.

In one exemplary embodiment, the joining unit includes a joining area and an observation unit, so that the chain assembly is viewable from the outside.

Advantageously, configuration of individual implants is thus visually traceable and can be corrected simply by opening the cover flap (possible up until the final joining of chain links).

Preferably, the observation unit is an indirect observation unit, so that the chain is indirectly viewable. It is particularly preferable that the observation unit has a mirror-lens unit.

Furthermore, the device can include a flap for opening the housing in the joining area of the joining unit.

Preferably, a needle holder is arranged at the end of the working channel and a first blocking element is arranged between the needle holder and joining unit.

The joining unit also includes a mandrel which is displaceable along the first axis in the working channel. The mandrel is preferably displaceable using a moveable external grip on the housing.

The device construction, with its working channel below the magazines and a mandrel in the working channel, prevents the mandrel from being bent due to incorrect operation.

The joining unit can also include a magnetic coupling, such that the external grip and the mandrel are separable from each other if a force threshold value is exceeded.

The mandrel and the at least one means for ejecting chain components are preferably coupled to one another via a second locking element, such that after one-time actuation of the ejection means the ejection means cannot be operated a second time until the mandrel has been displaced.

The receiving devices preferably include safety mechanisms for latching, securing and releasing magazines with chain components.

The device can include a third blocking element, which, in its locked state, only allows the mandrel to be moved to a certain point where the chain components are not yet assembled in the working channel. The third blocking element is preferably connected with the first blocking element between the needle holder and the joining unit so that the first blocking element in the needle holder can only be unlocked once the third blocking element is unlocked. The receiving devices can contain encoding elements which are configured to cooperate with corresponding encoding elements of a magazine so that a receiving device can only be used with a specific type of magazine.

A system for joining chain components to a chain with radiation sources is also proposed, which has a housing, a working channel that extends along a first axis of the housing, a loading unit connected with the working channel and including at least two receiving devices for chain component magazines, as well as at least one means for ejecting chain components from the received magazines. It also includes a first magazine for radiation sources which is arranged in one of the at least two receiving devices, a second magazine for additional chain components different from the radiation sources and arranged in the other of the at least two receiving devices. The device also includes a joining unit for assembling chain components. The working channel does not pass through the magazines. The first magazine for the radiation sources and the second magazine for additional chain components are spaced along the first axis and positioned vertically above the working channel. This allows the chain components to be ejected downwards into the working channel.

BRIEF DESCRIPTION OF THE DRAWINGS

Exemplary embodiments of the invention are explained in the drawings and following descriptions. It is shown in.

DETAILED DESCRIPTION OF THE INVENTION

The present invention describes a device and system for assembling chain components to a chain that contains radiation sources. The device is used in the manufacture of chains made from radiation sources and spacers for treatment of prostate cancer. It can also be used for manufacturing chains with radiation sources to treat breast cancer. The needles can also be loaded with titanium seeds. Hereinafter, the spacers and radiation sources have connection elements so that chains can be manufactured through a mechanical connection.

Figure 1:
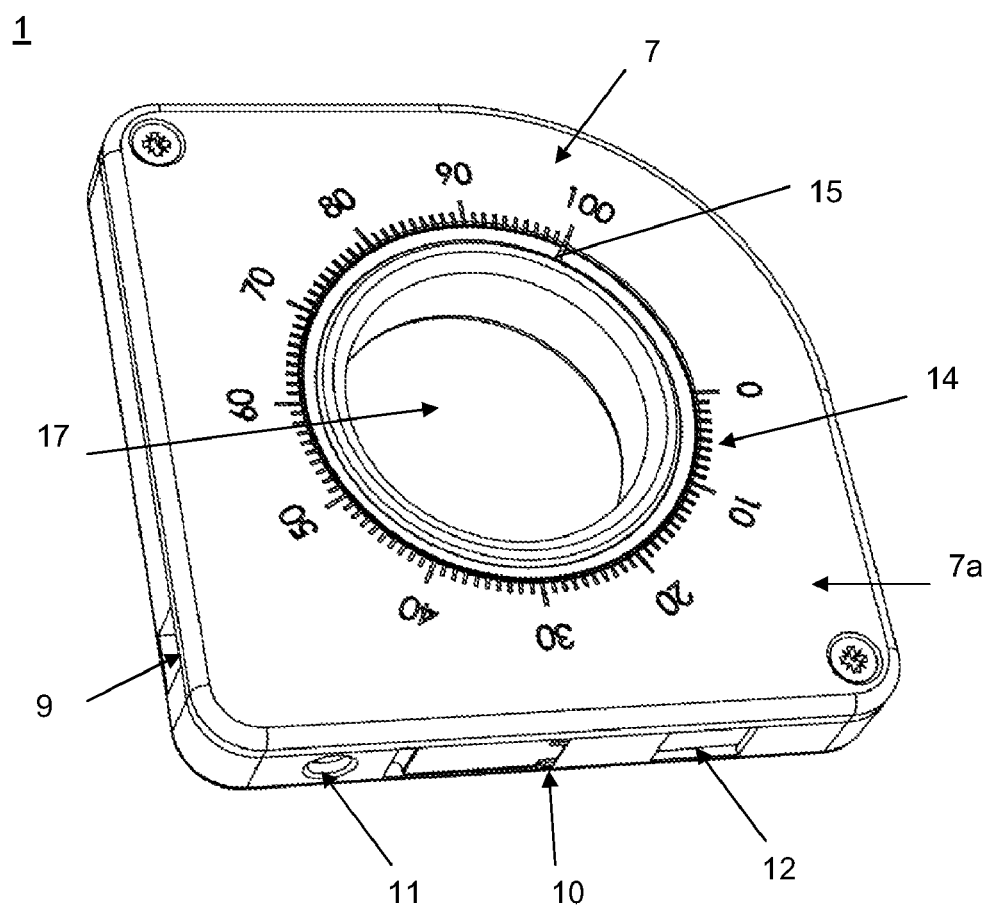
FIG. 1 a top view of a magazine according to the invention for chain components of a chain with radiation sources, FIG. 2 a top view of a magazine according to the invention for chain components of a chain with radiation sources without a cover, FIG. 3 a top view of a magazine according to the invention for chain components of a chain with radiation sources without a cover, without a receiving device for chain components and without a sprocket, FIG. 4 a core magazine components without the housing, FIG. 5 a vertical section through the magazine of FIG. 1, FIGS. 6-11 the ejection mechanism according to the invention in various steps, FIG. 12 the blocking mechanism according to the invention in the magazines.
Figure 2:
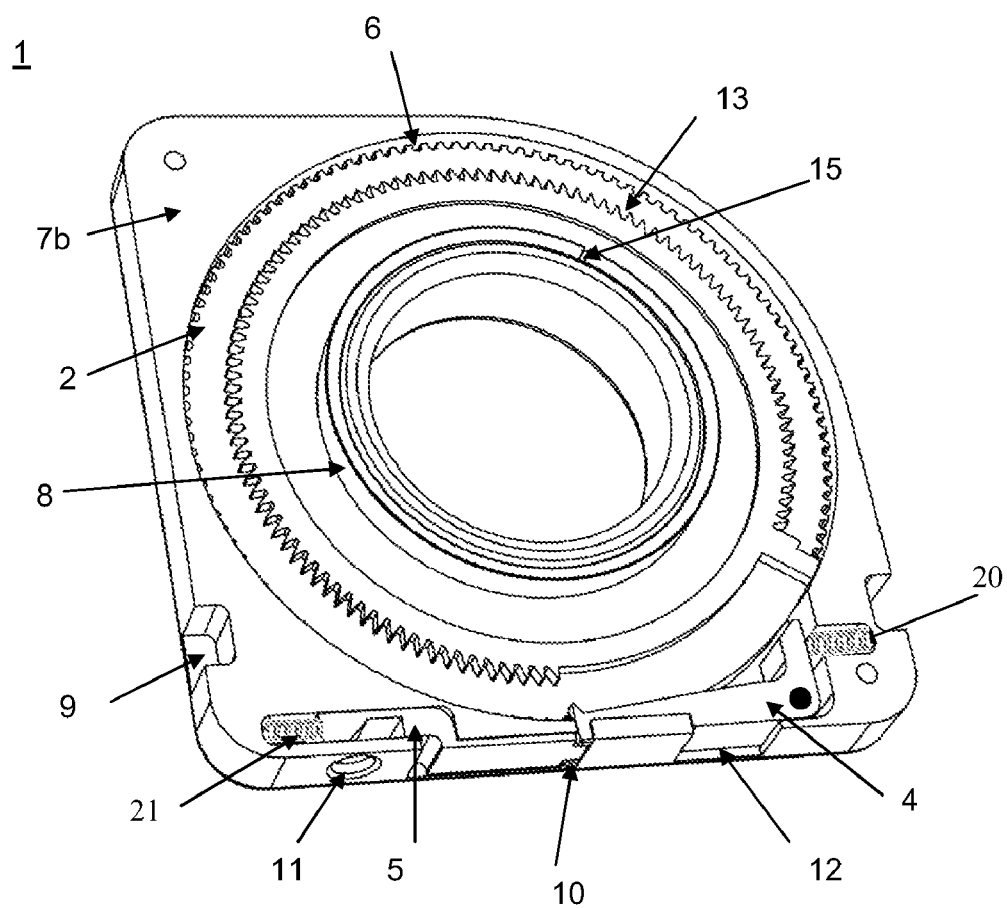
Figure 3:
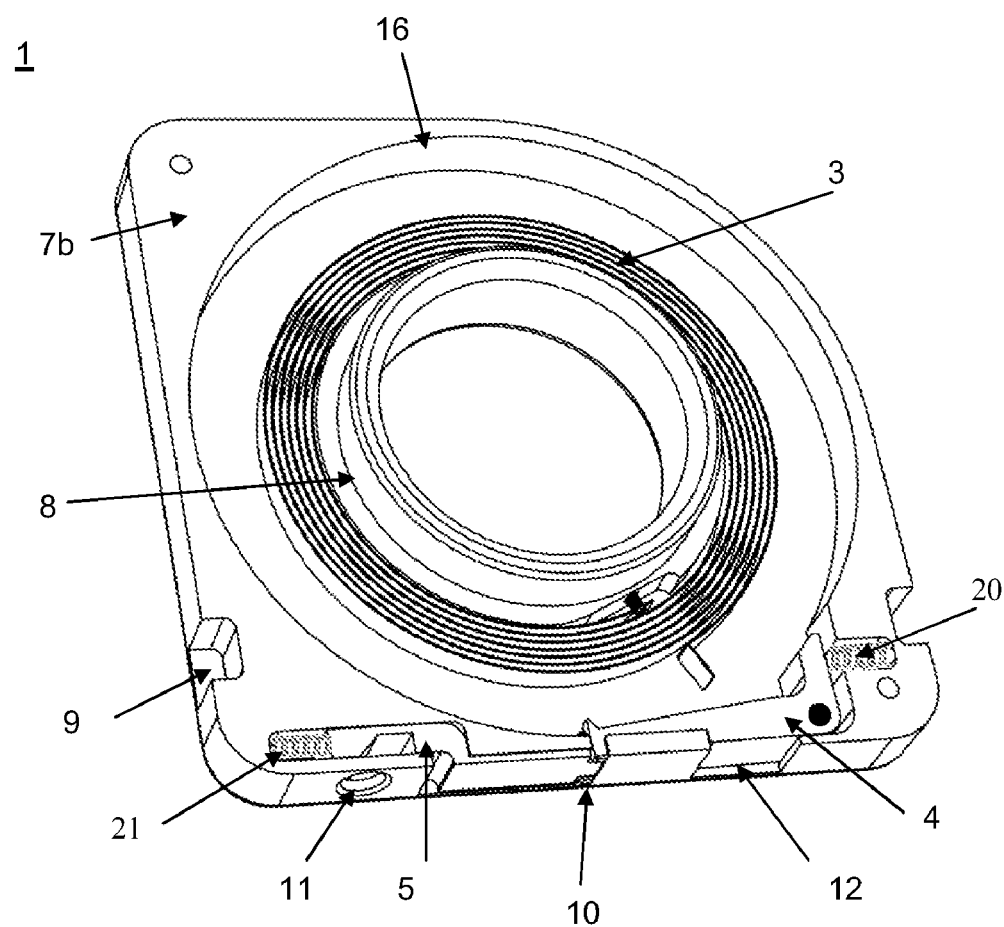
Figure 4:
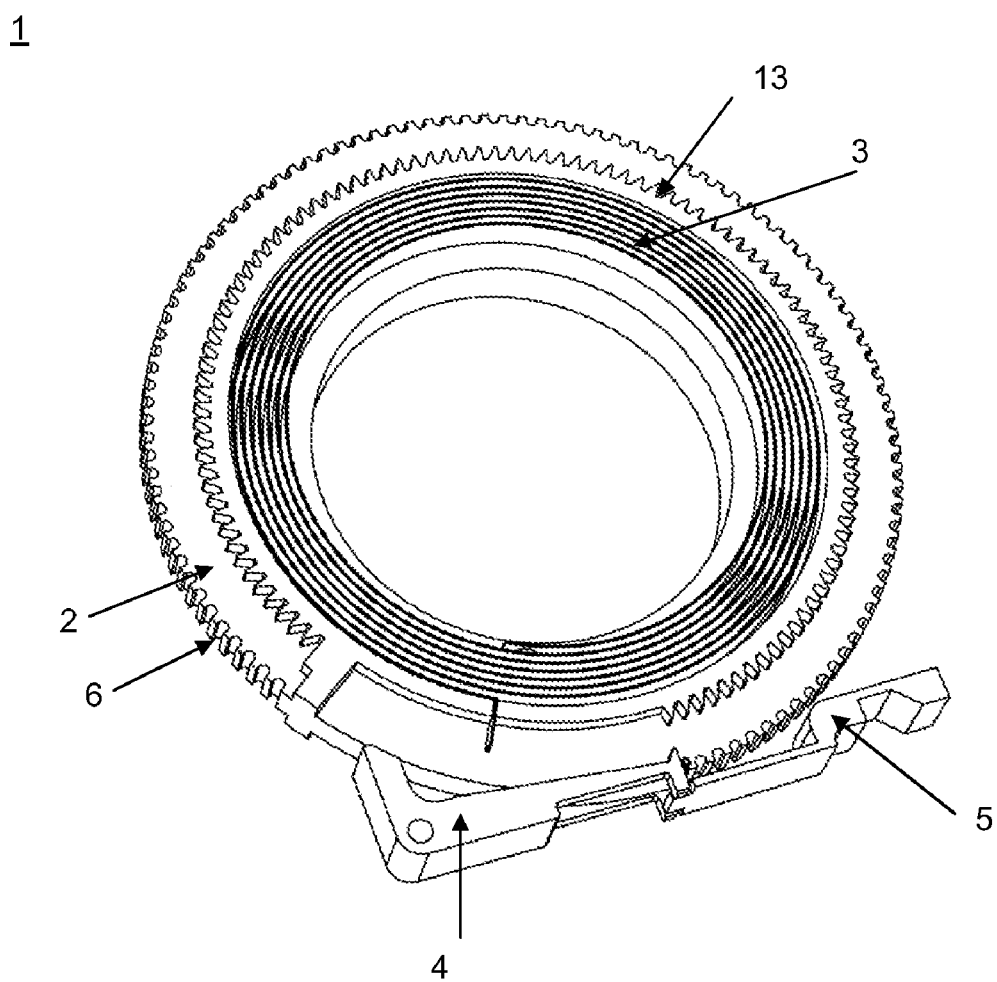
Figure 5:
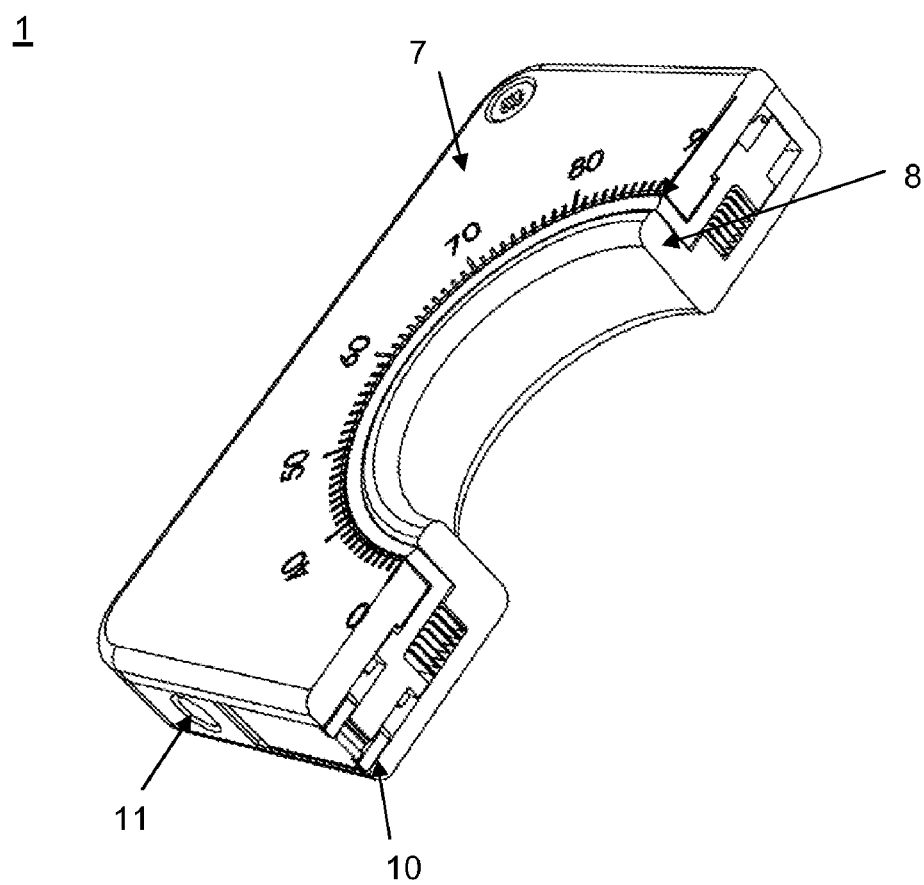

FIG. 1 shows a top view of a magazine (1) according to the invention for chain components of a chain with radiation sources. FIG. 2 shows a magazine without a cover (7a). In FIG. 3, a receiving device for chain components (2) and a sprocket (13) have been omitted. FIG. 4 shows the core components of the magazine without housing (7), and FIG. 5 shows a vertical section through the magazine of FIG. 1.

As shown in FIGS. 1 and 2, the inventive magazine (1) includes a housing (7) consisting of a cover (7a) and a housing shell (7b). The cover includes a display (14) for displaying the magazine's fill level in conjunction with a marking (15). The marking is preferably arranged on an interior bearing ring means used to receive chain components (2).

An encoding bore (11), an ejector (10) and a first opening (12) are arranged on the periphery of the magazine (1), preferably on the lower sidewall of the housing (7). Preferably, only one ejector or ejector opening (10) is provided so that the radiation exposure can be held to a minimum when using the radiation sources as chain components. Ejection thus occurs in the same or a parallel plane where the means for receiving chain components rotates. The chain components are ejected away from the magazine. After the chain component has left the ejector, there is no more contact between the magazine and the chain component. The encoding bore (11) and/or ejector (10) and/or the first opening (12) are preferably arranged separate from and below the means for receiving chain components (2), but in the same plane or in a parallel plane.

In a preferred exemplary embodiment, the magazine is configured for exactly one type of chain component, either for radiation sources or for spacers. Thus, it is impossible to confuse the ejected chain components.

An ejection lever (4) which is rotatably mounted in the housing (7) is arranged in conjunction with the first opening (12). The ejection lever (4) is actuated from the outside through the first opening (12). In the rest position, the ejection lever (4) closes the ejector (10) from the inside. The ejector (10) is also connected with a locking slider (5) which closes the ejector (10) to the outside by the force of a second tension spring (21). The locking slider (5) is translationally displaceable so that the ejector (10) is deblocked when the locking slider (5) is actuated. The locking slider (5) can be actuated via an opening (11) or the encoding bore (11) in order to deblock the ejector (10). Furthermore, the magazine has preferably, but not as a limitation, a central opening (17). As seen in FIG. 2, a circular means for receiving chain components (2), also referred to as a "seed depot" (2) when speaking of a magazine for radiation sources, is inserted and rotatably supported in the rear housing shell (7b). The means for receiving chain components (2) includes radially arranged depressions (6) which are designed to receive chain components, such as radiation sources (19) or spacers (18), and prevent them from a falling out. The depressions (6) are preferably designed to match the shape of the chain components. It is particularly preferable that the depressions (6) have a semicircular shape and are provided on the circular edge along the periphery of the means for receiving chain components (2). In other words, the means for receiving chain components (2) resembles a gear wheel, but, has depressions (6) on its outer edge instead of teeth. A tension spring (3), preferably a constant-force spring (3), enables advance of the means for receiving chain components (2) concentrically with its center. Thus, no external driving force of the magazine is required for ejecting a chain component. The magazine can be completely sterilized. Only an external impulse on the ejector lever is required to eject a chain component so that the drive can be operated independently in the interior. A material wall from the housing (7) serves as the bearing surface in form of an interior bearing ring (8) for the means for receiving chain components (2). The interior bearing ring (8) is preferably formed around the opening (17). Furthermore, a sprocket (13) which preferably has a smaller diameter than the means for receiving chain components (2) is arranged on the means for receiving chain components (2). The sprocket (13) is operatively connected to the means for receiving chain components (2) or is directly connected to the constant-force spring (3) and is also rotatably supported in the housing (7). The sprocket (13) is connected with the means for receiving chain components (2) with a rotation lock, which is designed to limit the advance of the constant-force spring (3) during ejection so that only a single chain component can be ejected at one time. Preferably, the sprocket (13) and means for receiving chain components are formed in one piece.

Starting from the center of the magazine (1) proceeding towards the outside, the magazine (1) consists of a central opening (17), an interior bearing ring (8), the sprocket (13), the means for receiving chain components (2) and a boundary (16) of the means for receiving chain components (2). In the present exemplary embodiment, the sprocket (13) and the means for receiving chain components (2) are embedded into a depression of the rear housing shell (7b).

The inner wall (16) of the depression (see FIG. 3) serves to limit the means for receiving chain components (2). The distance between the wall (16) of the depression, or more generally, between the boundary (16) of the means for receiving chain components (2) and the means for receiving chain components (2) itself, is sized in such a way that the chain components can be are guided and held captive in the depressions (6). The chain components are hereby guided on a circular path towards the ejector (10). The tension spring (3) is supported below the means for receiving chain components (2), as seen in FIG. 3.

As described below, the ejection lever (4) inhibits the spring (3) and therefore the means for receiving chain components (2). Inhibition of the spring (3) and the means for receiving chain components (2) allows only the release of a single implant or chain component from the magazine for each magazine actuation. Inhibition takes place, on one hand, by positive locking of the first implant on the ejector lever (4) and, on the other hand, by the cyclical engagement of the upper sprocket (13). The ejector lever (4) also supports release of the implant by actively pushing the implant into a working channel. The ejector lever (4) is preferably springily supported and is actuated using a corresponding lever mechanism in the loading device (101) described below. The implants are released from the opening (10) at the magazine base into a working channel. The magazines (1) are preferably mechanically encoded and color-coded. The color-coding can be performed by coloring the means for receiving the chain components (2), which represents the moveable component of the scale. The number of spent radiation sources and spacers can be read directly on the magazines.

The following is a description of the magazine, exemplified using a radiation source magazine. This, however, is not a limitation. The discussion also applies to spacer magazines, unless anything to the contrary is explicitly mentioned.

To assemble the magazine (1), the tension spring (3) is first mounted to the rear half of the housing and is then inserted together with the means for receiving chain components (2) in the rear housing shell (7b). Subsequently, an ejector lever (4) and a locking slider (5) are used and tensioned, preferably using tension springs 20 and 21, as shown in FIG. 3. Here, the ejector lever (4) is rotatably mounted via a pin and the locking slider (5) can be translationally displaced in a groove in the housing shell (7b).

After assembling the magazine (1) without the cover (7a), the radiation sources (19) (or the spacers (18)) are positioned parallel to the axis of the means for receiving chain components (2) in the semi-circular depressions (6) on the front side of the means for receiving chain components (2). Before loading the means for receiving the chain components (2), the tension spring (3) must be tensioned, preferably using a constant-force spring (3). This is done by rotating the means for receiving chain components (2) in the tensioning direction of the tension spring (3). Inserting the first radiation source (19) prevents the tension spring (3) from relaxing.

The additional radiation sources (19) are subsequently inserted. In the subsequent operation of the magazine (1), the respective first radiation sources (19) serve (before their release) as a blocking element or as means to prevent the tension spring (3) from relaxing. After the magazine (1) is filled, a cover (7a) is applied. An inner bearing ring (8) of the means for receiving chain components (2) is widened and serves, when provided with a marking (15), in conjunction with the magazine cover (7a), as a content indicator for the radiation sources (19) or spacers (18) remaining in the magazines.

With the exception of the locking slide (5) and the respective milled-out portion in the rear housing shell (7b), the magazine (1) for storing the spacers (18) is identical to the radiation source magazine. Therefore, assembling and filling both types of magazines are done similarly. The locking slider (5) can also be arranged in the spacer magazine. However, this is not absolutely necessary because the spacers are not radioactive. The locking slider (5) from the radiation source magazine serves to shield the radiation towards the outside before the magazine is inserted into the device (101) for filling.

At least one, preferably both, of the narrow sides of a magazine (1) are provided with locking grooves (9). These serve, after installation of the magazine (1) into a device (101) for assembling radiation sources, to hold them captive in the device as well as a positioning aide for a working channel in device (101).

In the center region of the bottom surface of the radiation source magazine there is an opening for ejecting the implants (10). The side on one side of this opening (10) is provided with an encoding hole (11). When installing the radiation source magazine into a device for joining radiation source chains (101), the locking slider (5) is displaced by an encoding bolt in the device (101) so as to release the ejection opening (10). This function is preferably not implemented in the spacer magazine, since the locking slide (5) is supposed to prevent exposure of the operator to radioactive radiation from the radiation sources (19). This is not necessary for the spacers (18), since these are not radioactive. Of course the slider (5) can still be provided.

Figure 6:
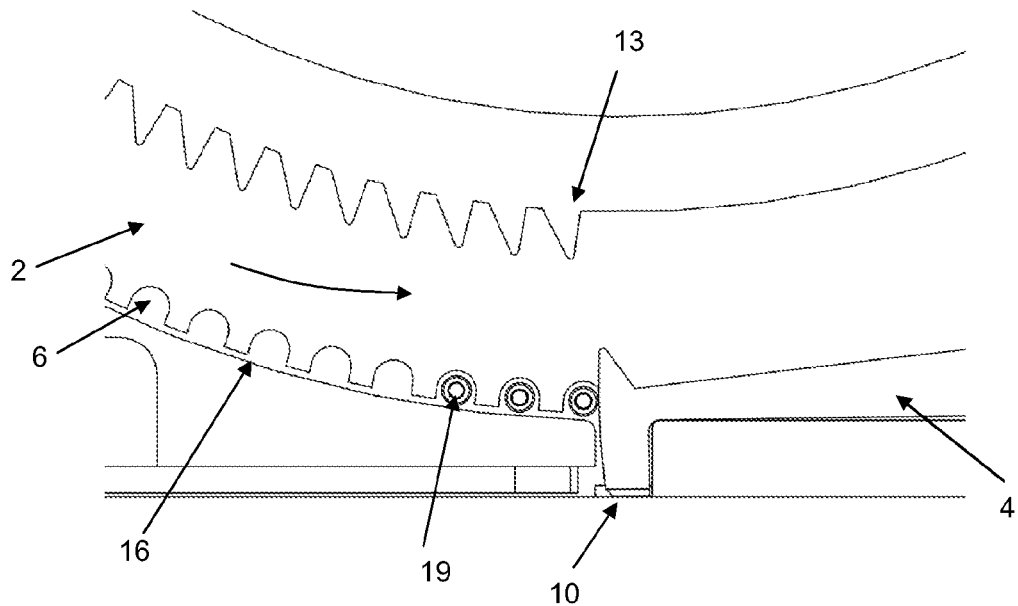
Figure 7:
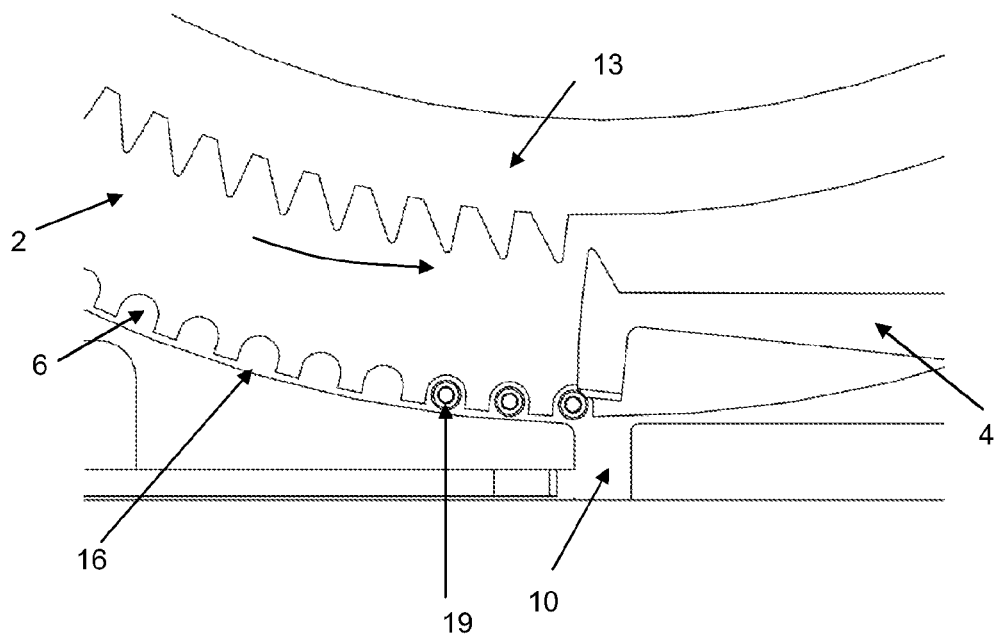
Figure 8:
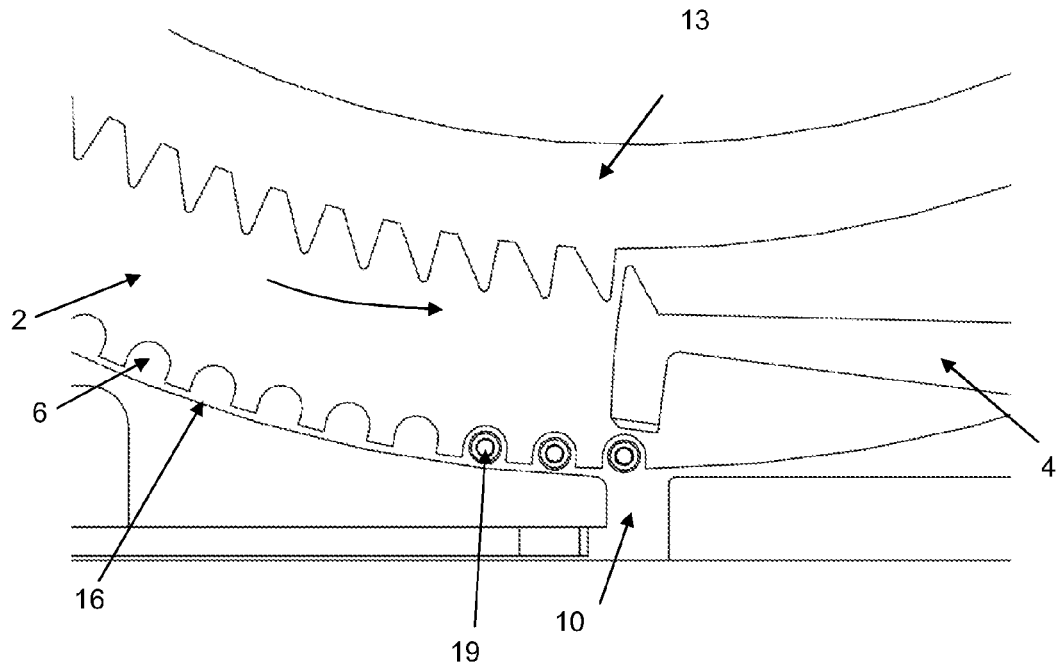
Figure 9:
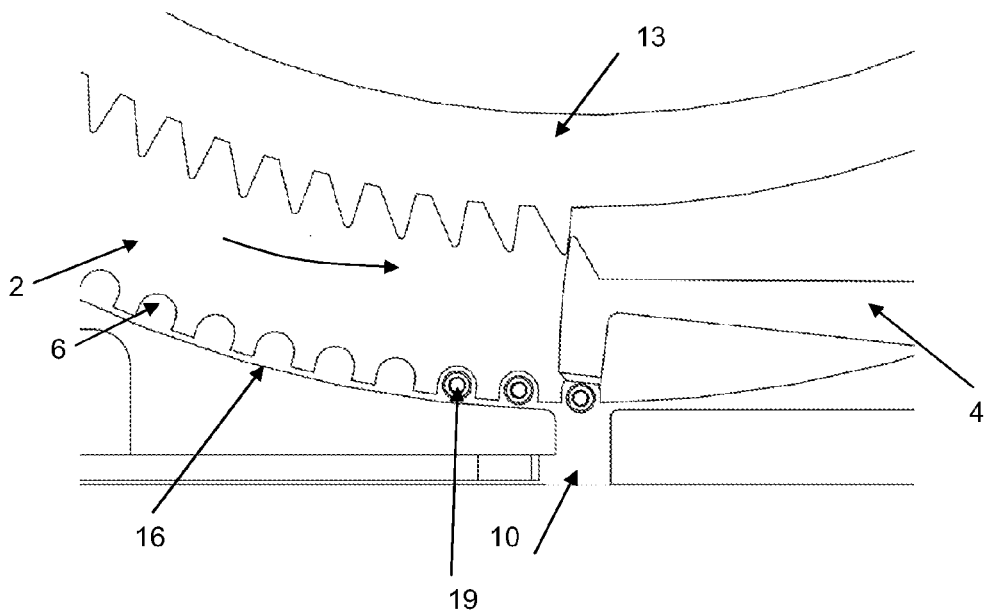
Figure 10:
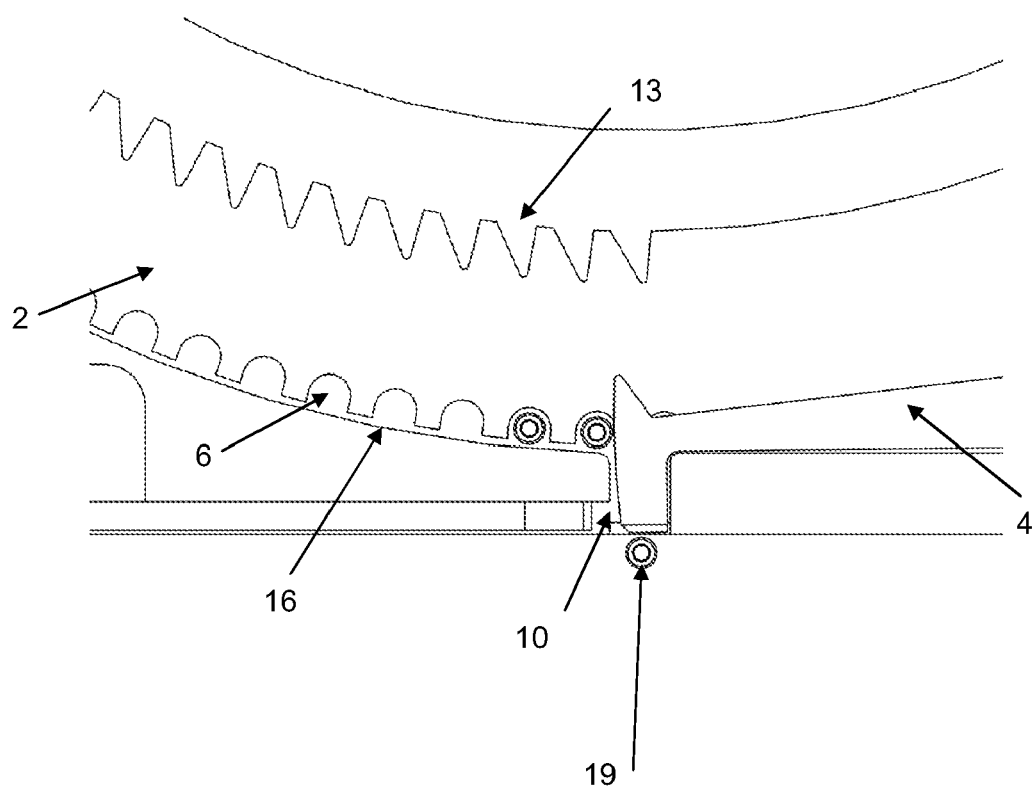
Figure 11:
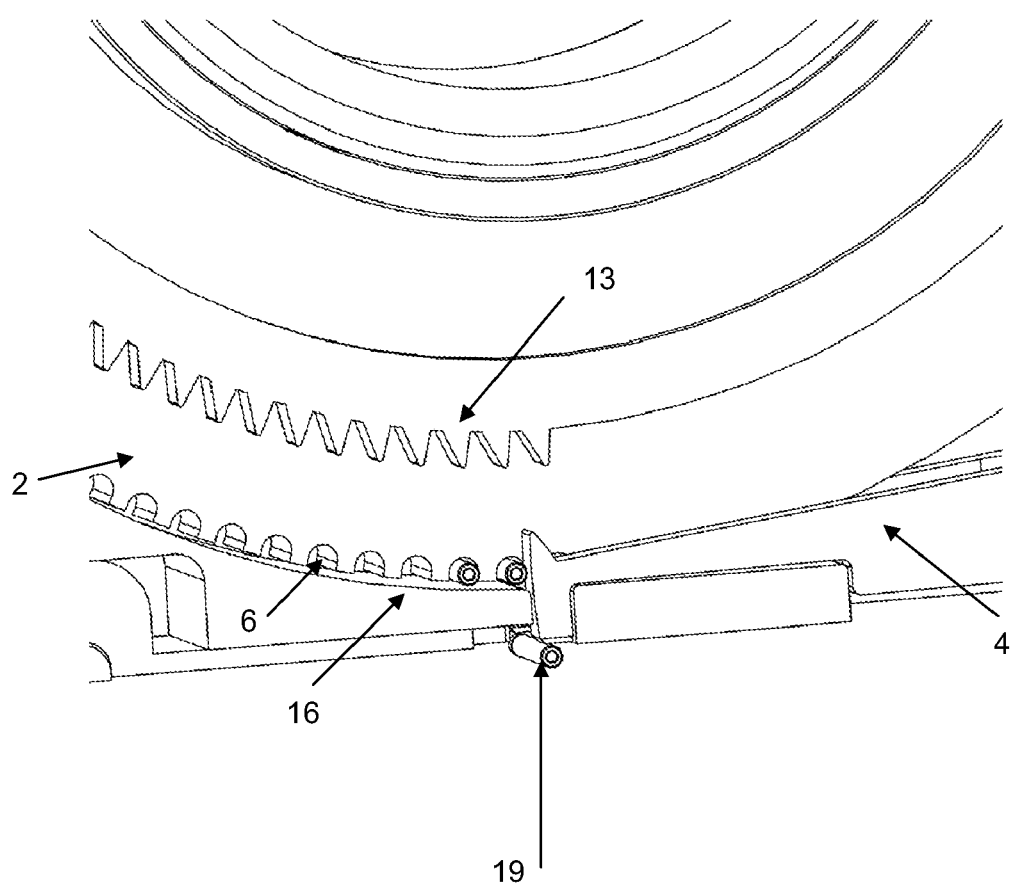
Figure 12:
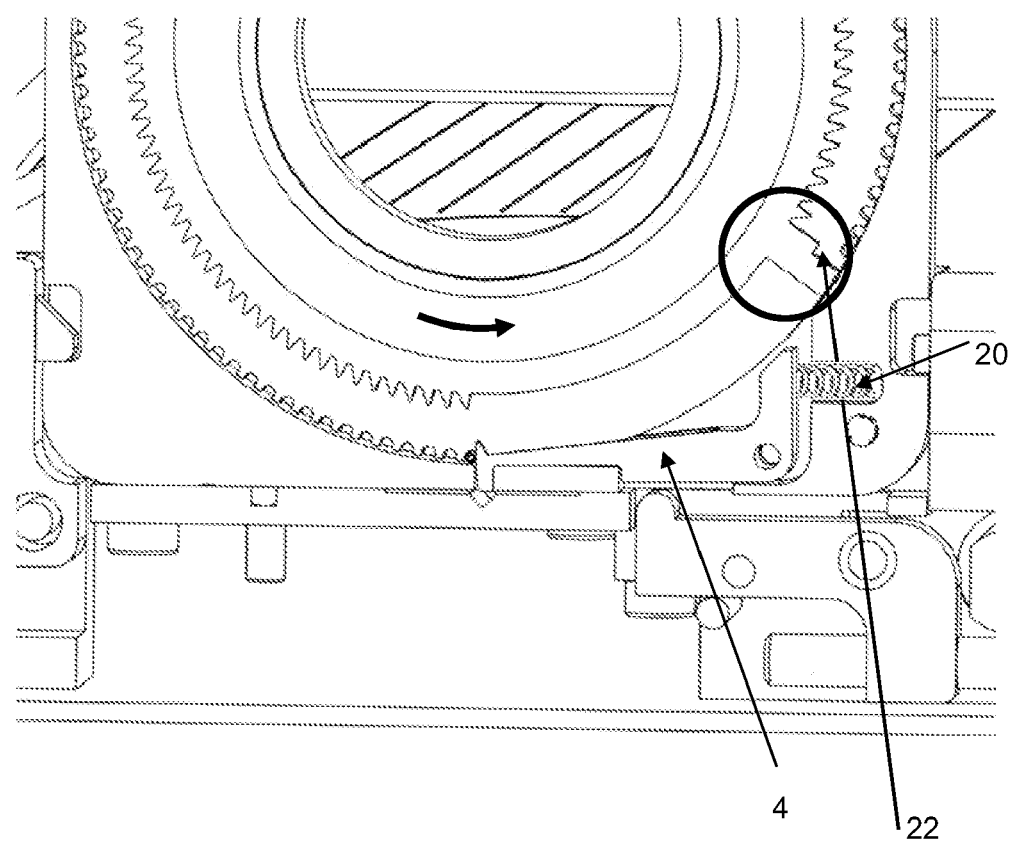

The ejector lever (4) can be operated via a corresponding lever mechanism (113) in the device (101) through a second opening (12) on the other side of the ejection opening (10). The ejection mechanism is illustrated in individual steps in FIGS. 6 through 11. Initially, the ejection opening (10) is physically blocked by the ejector lever (4), as illustrated in FIG. 6. In this position, the ejector lever (4) does not engage with the sprocket (13). A single radiation source (19) or a spacer (18) are ejected from the magazine (1) by operating the outer surface of the ejector lever (4), which causes the ejector lever (4) to slide up towards the first radiation source (19) or the first spacer (18) (FIG. 7). The first radiation source (19) or spacer (18) loses its blocking function depicted in FIG. 6, the means for receiving chain components (2) moves, driven by the tension spring (3), concentrically to the central opening (17) or the center of the magazine (1). However, this motion is blocked during further movement by the engagement of the ejector lever (4) with the gears of the upper sprocket (13) of the means for receiving chain components (2) (FIGS. 8, 9). This rotation of the means for receiving chain components (2) pushes the first radiation source (or spacer), and only it, into a position located above the ejection opening (10) (FIG. 9). The first radiation source is then released downward towards the rear via the ejector lever (4), preferably into a working channel (not shown) below the ejection opening (10) for the assembling the chain components (FIGS. 10 and 11). After operating the ejector lever (4), the ejector lever returns to its previous position and blocks the ejection opening (10) again, as shown in FIG. 6. This again prevents further rotation of the means for receiving chain components (2) due to the abutment of the next first radiation source (19) or the next first spacer (18) on the ejector lever (4) (FIG. 11). This mechanism incrementally rotates the means for receiving chain components (2) and makes a single ejection of the radiation source (19) or spacer (18) into a working channel possible. Release of the lever 4 for magazine operation of empty magazines (1) is not possible. This is illustrated in FIG. 12. An arrow shows the rotation direction of the means for receiving chain components (3). The last magazine implant is arranged at the location indicated with a circle. After the last implant is ejected from the magazine, the lever (4) falls into the circled trough of the blocking element (22) forced by the tension spring (3) and the lever spring, and the first compression spring (20). The blocking element (22) does not offer room for movement of the lever (4). Operation of the buttons (113a) of the lever mechanism (113) for ejecting chain components (see FIG. 18) causes an excursion of the lever (4) via a lever mechanism (113). However, because this movement is blocked, operation of the buttons (113a) is also blocked with an empty magazine.

Figure 13A:
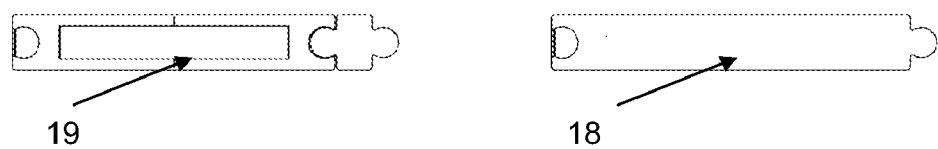
FIG. 13a shows an external longitudinal cross-section of spacers and radiation sources and FIG. 13b shows a perspective view of the spacers and radiation sources configured for joining into a chain, FIG. 14 a perspective view of the inventive device for joining and assembling chains containing radiation sources.
Figure 13B:
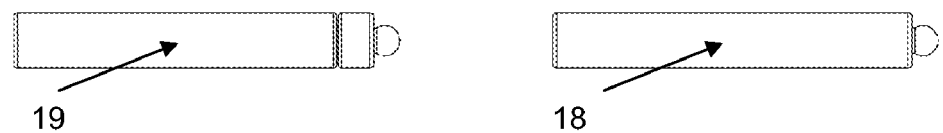

FIG. 13 shows spacers (18) and radiation sources (19) configured for assembly. FIG. 13a shows an external, longitudinal cross-section of the spacers (18) and radiation sources (19). The radiation sources (19) have an interior radioactive core, illustrated as a rectangle in FIG. 13a. The radiation sources (19) and spacers (18) have ends configured for joining or assembly into a chain. Two spacers (18) or two radiation sources (19) can also be joined together. The spacers (18) or radiation sources (19) preferably each have male ends (right) and female ends (left). The chains can be freely assembled due to the design of the radiation sources (19) and spacers (18).

Figure 14:
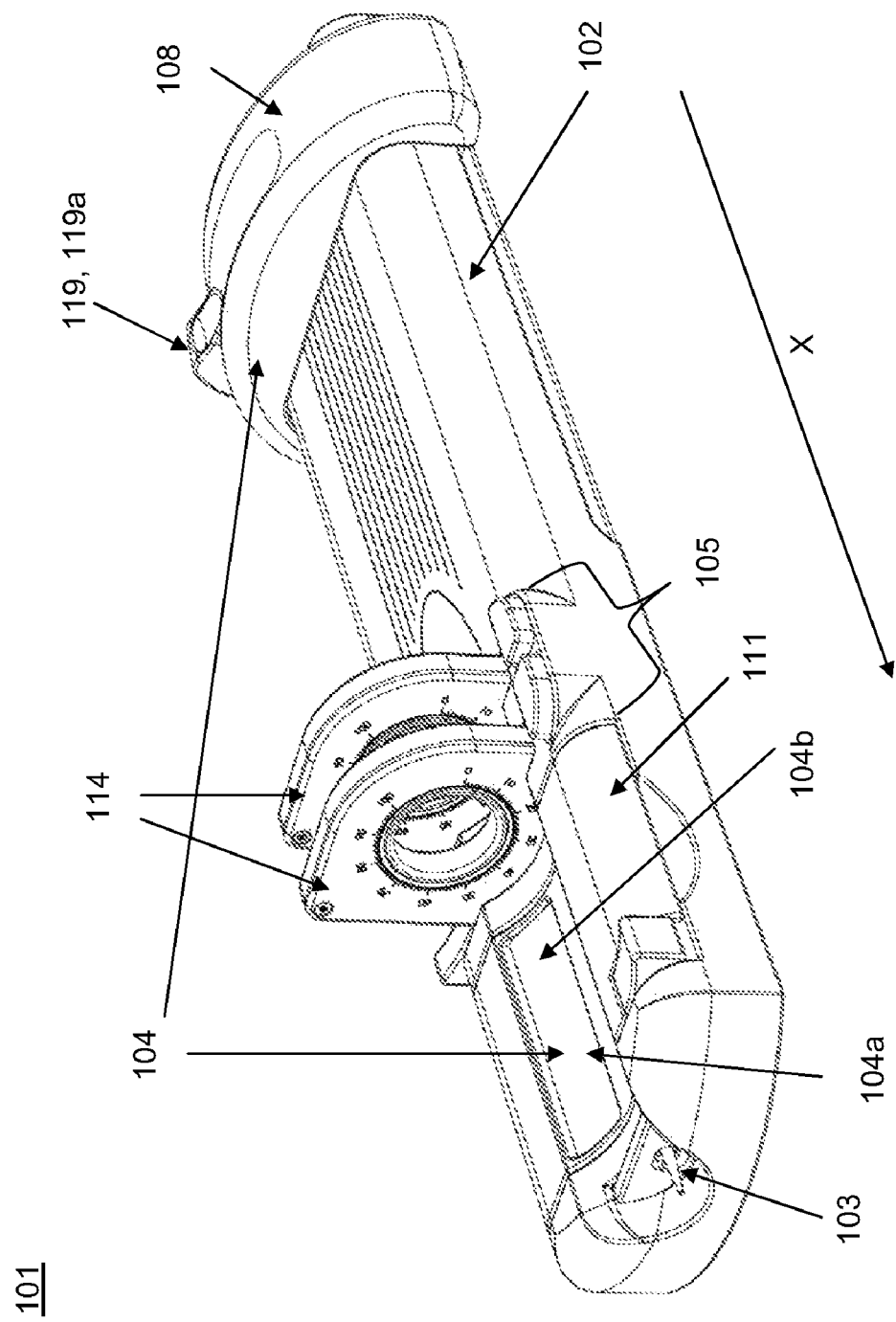

FIG. 14 shows a perspective view of a device (101) according to the invention for joining and assembling radiation chains with radioactive radiation sources, preferably operated with the magazines 1 described above.

Figure 15:
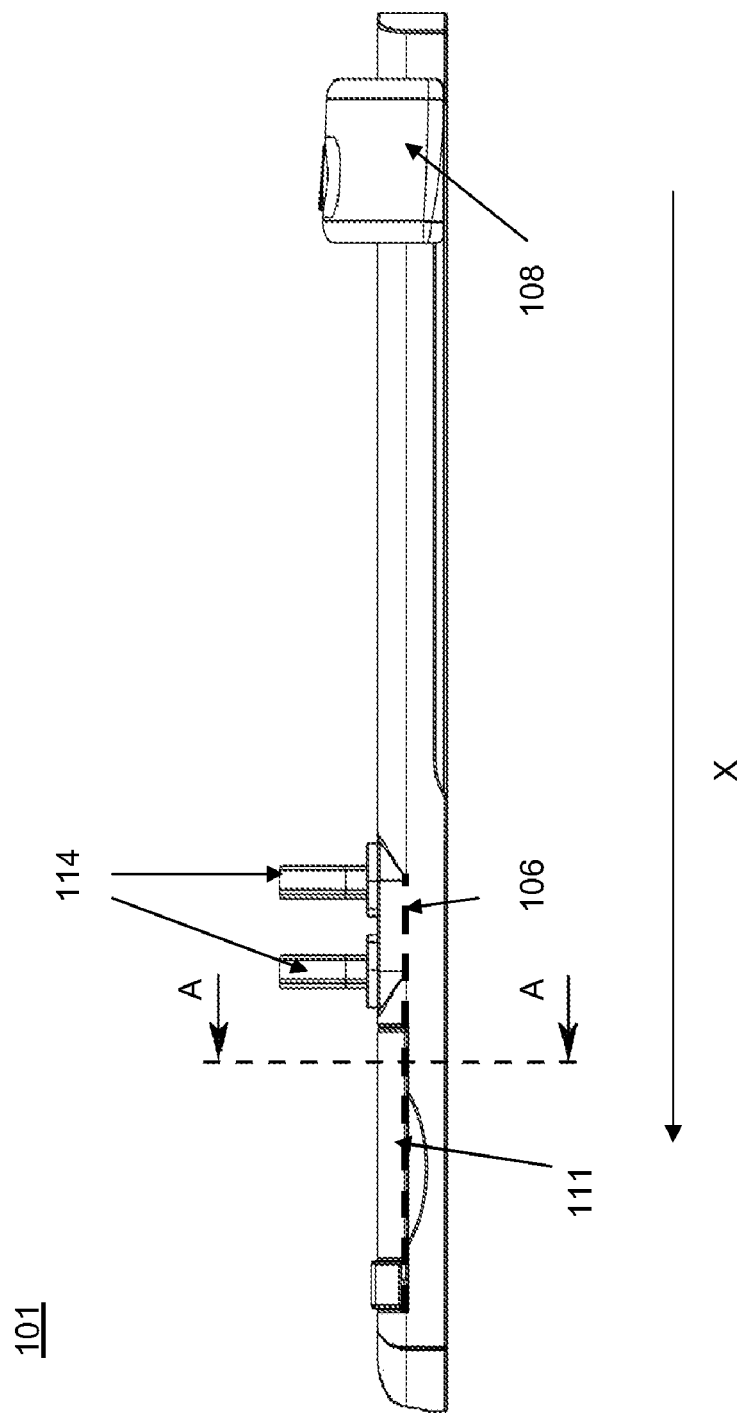
FIG. 15 a side view of the inventive device for joining and assembling chains of FIG. 14, FIG. 16 a perspective cross-section of the inventive device along the line A-A in FIG. 15, as seen in the direction opposite to the arrow in FIG. 15, FIG. 17 a cross-section through the inventive device along the line A-A in FIG. 15, as seen in the direction of the arrow in FIG. 15, FIG. 18 a first view of the inventive device without housing, FIG. 19 a second view of the inventive device without housing, FIG. 20 a cross-section of the joining device through a spacer magazine.
Figure 16:
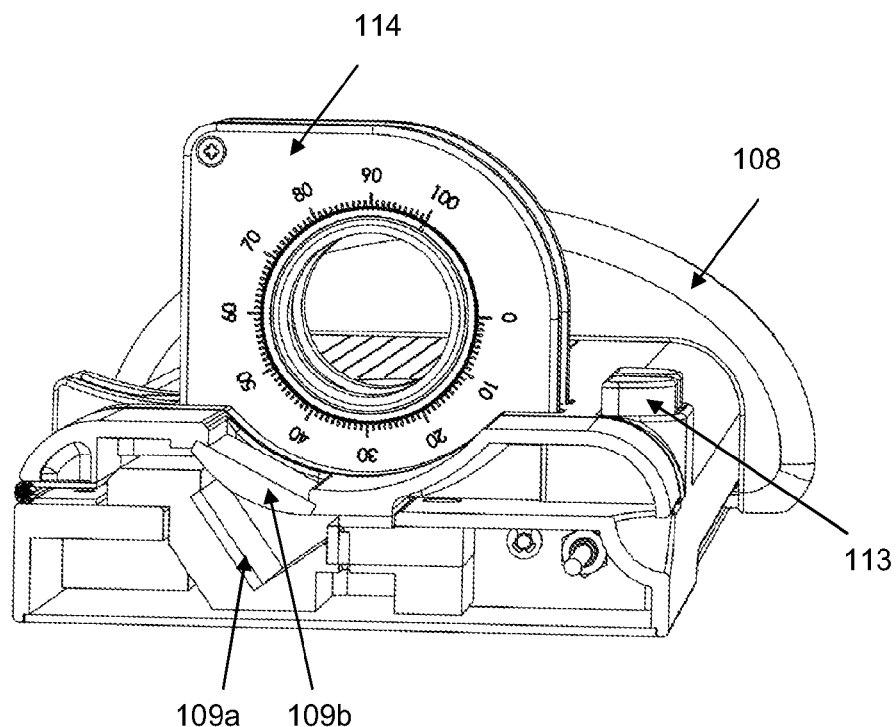
Figure 17:
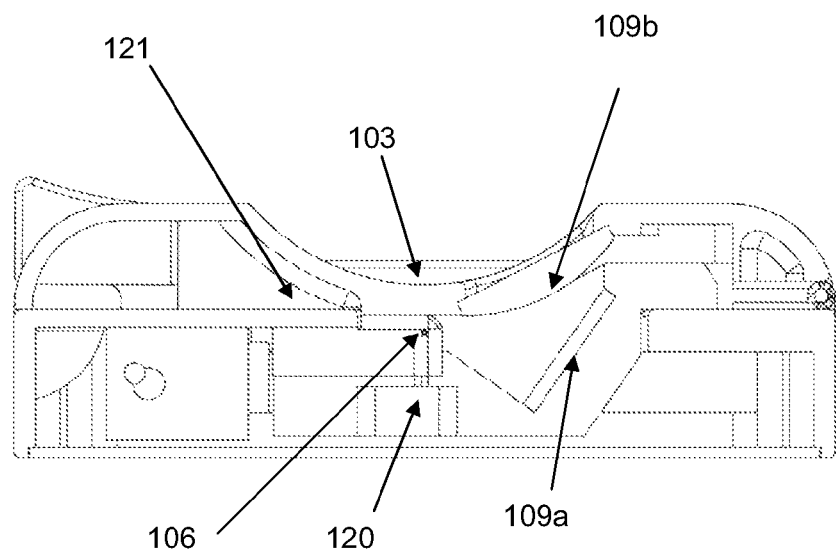
Figure 18:
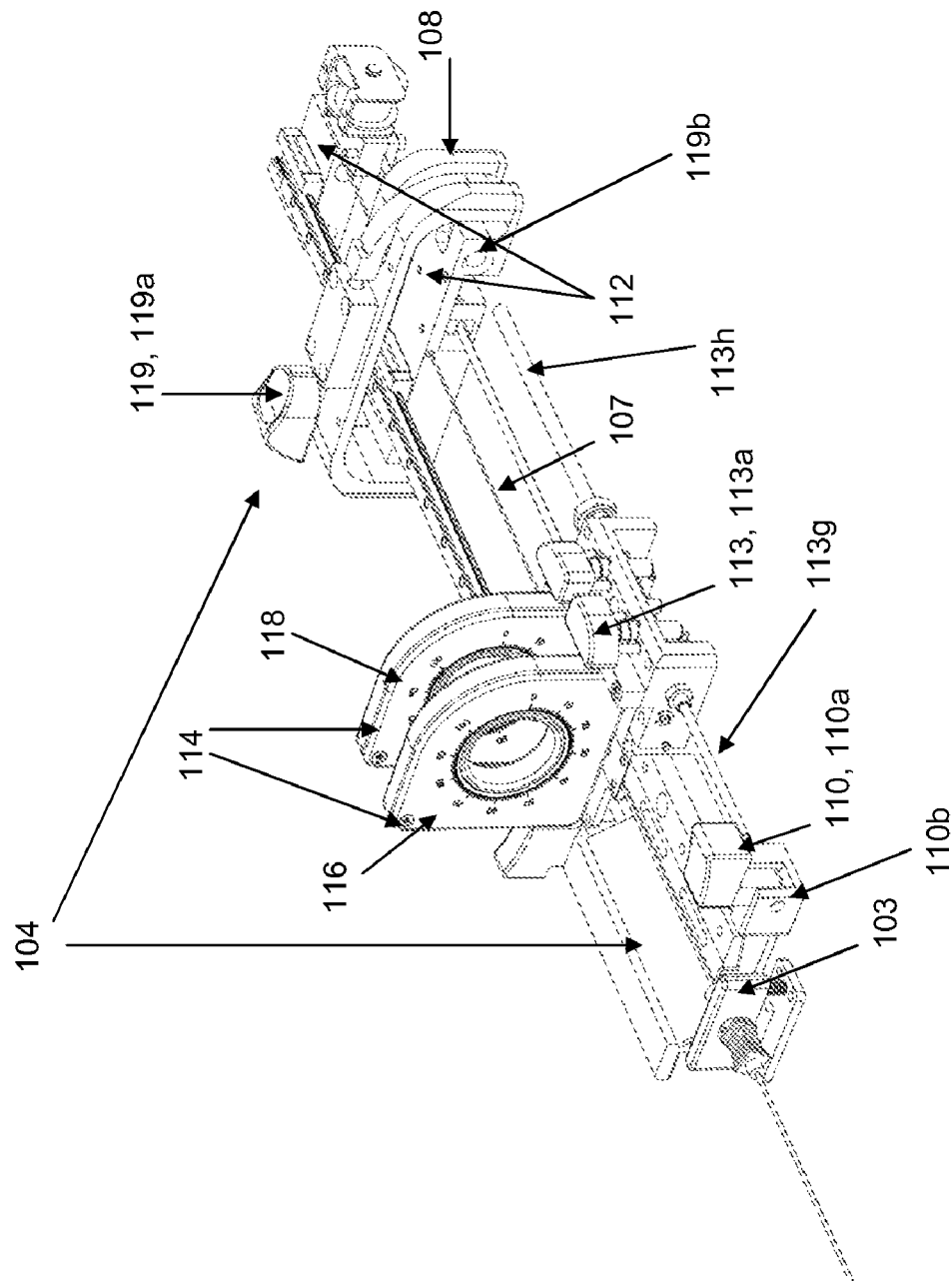
Figure 19:
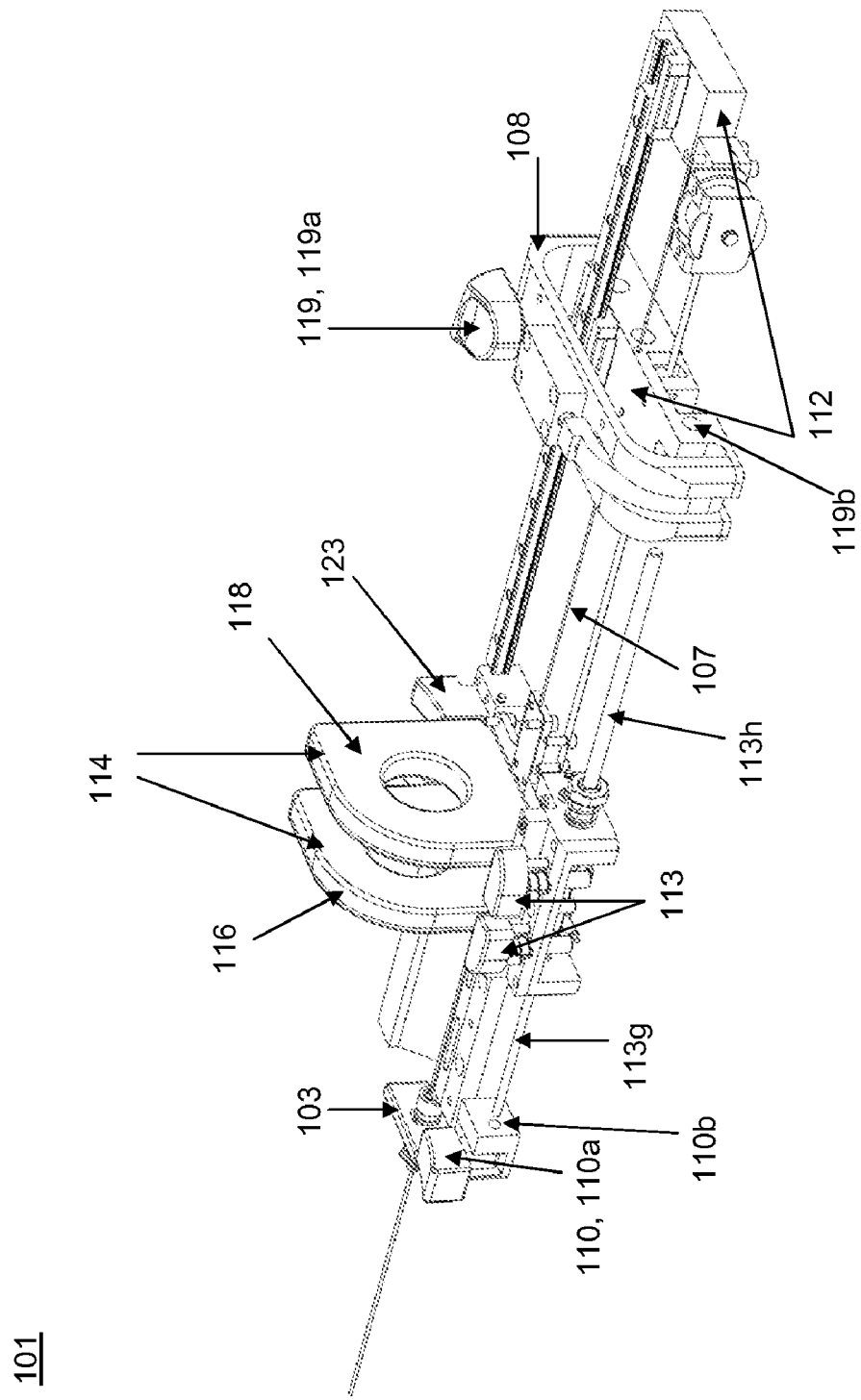
Figure 20:
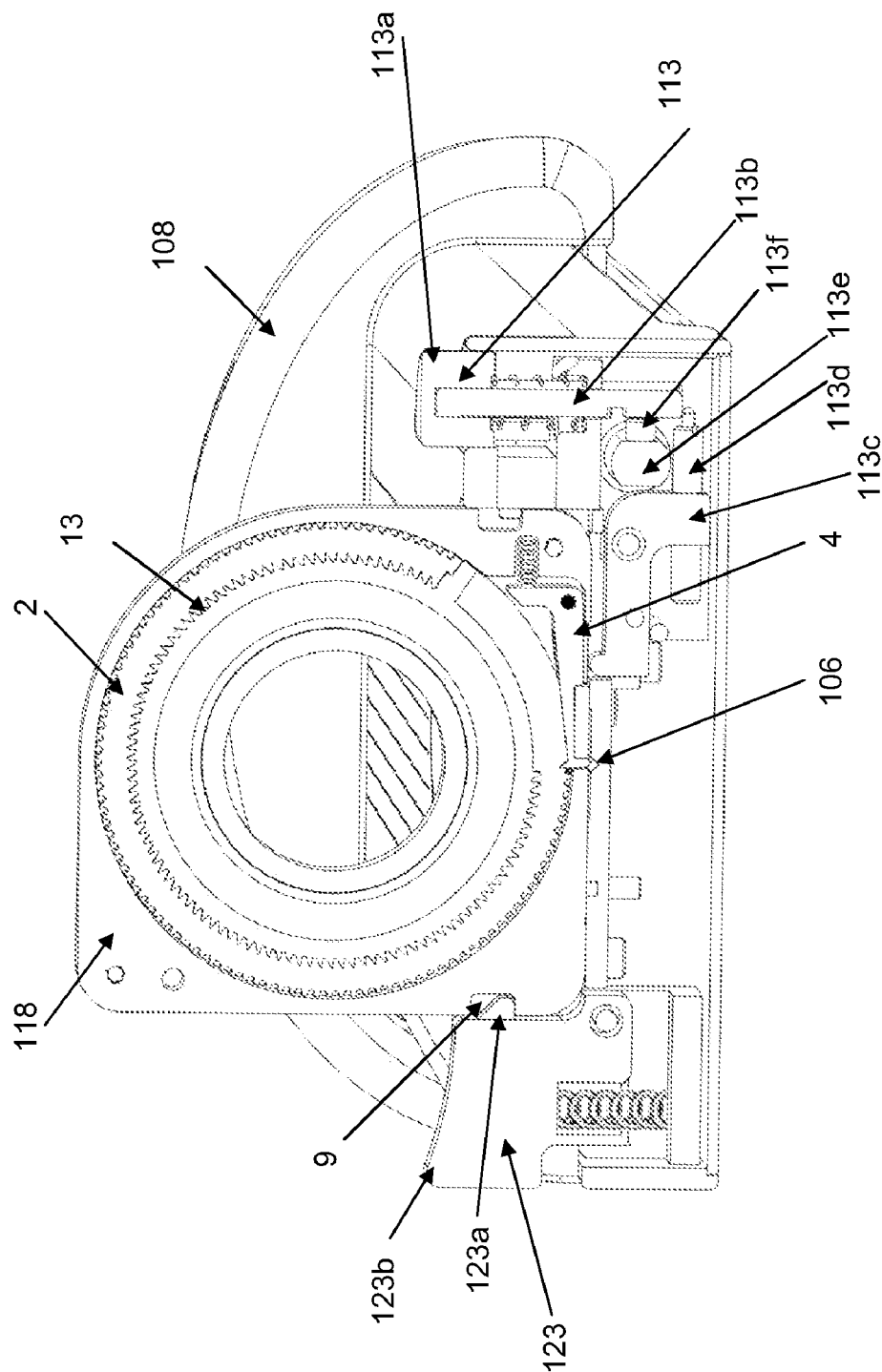
Figure 21:
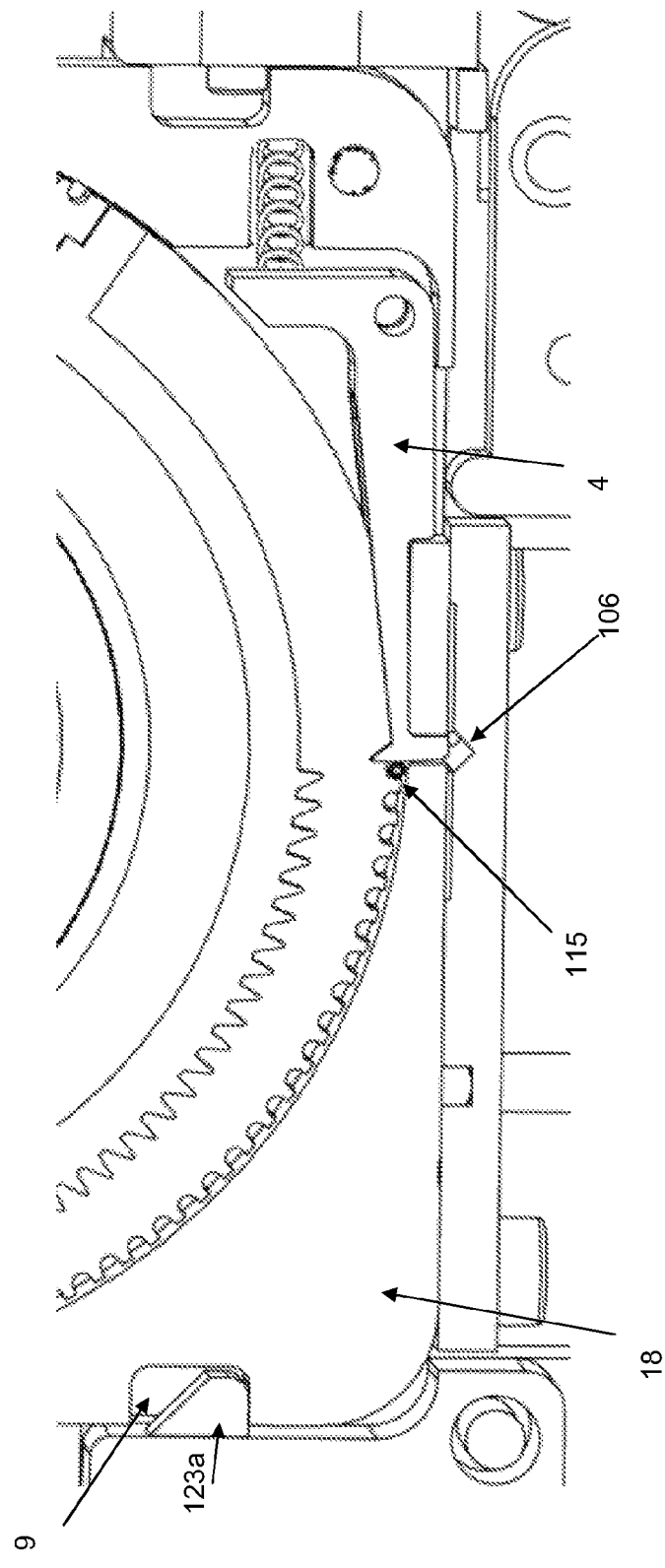
FIG. 21 an enlargement of FIG. 20 in the lower section of the spacer magazine.
Figure 22:
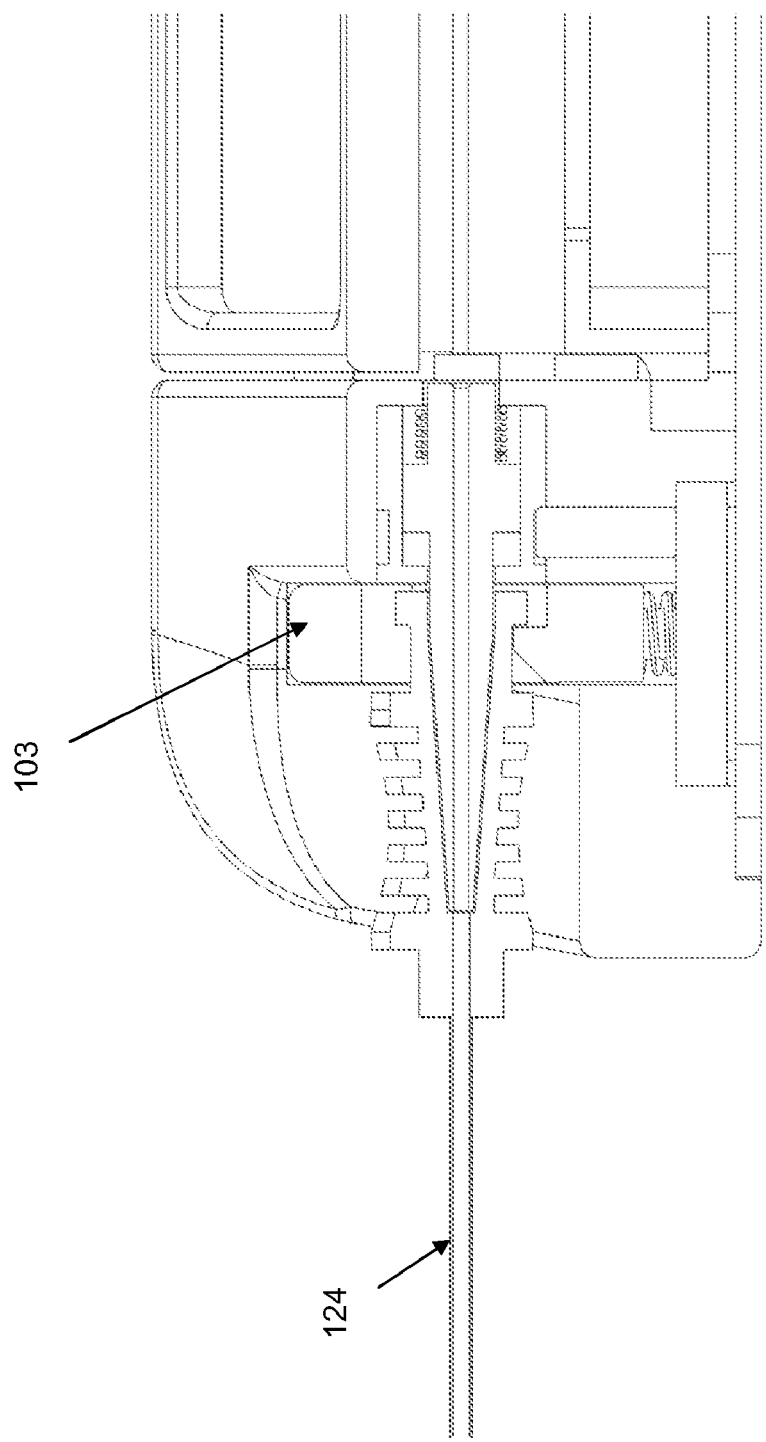
FIG. 22 a longitudinal section through the front section of the inventive joining device in the needle holder area.

FIG. 15 shows a side view of the device according to the invention for joining and assembling the radiation chains in FIG. 14. FIG. 16 shows a perspective cross-sectional view of the device according to the invention along the line A-A of FIG. 15, seen in the direction opposite to the arrows in FIG. 15. FIG. 17 shows a cross-section of the device according to the invention along the line A-A of FIG. 15, seen in the same direction of the arrows in FIG. 15. FIG. 18 is a first view of the device according to the invention without a housing. FIG. 19 is a second view of the device according to the invention without a housing. FIG. 20 shows a cross-section of the device for joining through a spacer magazine. FIG. 21 illustrates an enlarged view of FIG. 20 in the lower region of the spacer magazine. FIG. 22 shows a longitudinal section through the front region of the device according to the invention for joining in the region of the needle holder.

The device (101) according to the invention consists of a housing (102), a needle holder (103), a joining and observation unit (104) and a loading unit (105), as shown in FIG. 14. Magazines (114) for chain components are installed in the loading unit. The joining and observation unit (104) preferably includes a joining region (104a), where the chain components are joined, as well as a observation region (104b) for checking the arrangement of the chain components. In a preferred exemplary embodiment, the joining region (104a) can be reached from the outside via a flap (111). The needle holder (103) is arranged on one end of the device, whereas a handle (108) is arranged on the other, as described in more detail below. A lock (119) configured as a button element is arranged on the handle (108). The magazines (114) and the joining and/or observation regions (104a, 104b) are located between the handle (108) and the needle holder (103).

It is an object of the device (101) to assist with releasing radioactive radiation sources (115) and inactive spacers (117) from corresponding magazines (114), to join the implants (see FIG. 13) or chain components (115, 117) containing plug connections in form of a chain, and to then fill with them the needles (124) attached to the device (101) (see FIG. 22).

A central element of the aforedescribed device (101) is the working channel (106), which, as shown in FIGS. 15, 17, 19, and 20, extends along the X axis or a longitudinal axis of the device (101). The working channel (106), as seen from the handle, preferably starts closely before the magazine holders or, alternatively, exactly below the ejection opening of the magazine (114) closest to the handle and ends at the needle holder (113). The start of the working channel (106) closely before the magazine brackets enables better steering of the mandrel (107), as described later. The various units are arranged around the working channel (106), supported by the housing (102). The housing (102) supports and protects the other functional units of the device (101). FIGS. 14 and 15 show from right to left the handle (108), the magazines (114) with the loading unit (105), the joining and observation region (104a, 104b), and the needle holder (103).

The joining and observation unit (104) includes the working channel (106) and has a mandrel (107) (see FIG. 18 or 19), which is linearly guided by an external handle (108) in the working channel (106) as well as a minor-lens unit (109) (see FIG. 17) for viewing the implants in the joining region (104a). The mandrel (107) transports, via the handle (108) which can be laterally displaced by the user, the radiation sources (115) or spacers (117) released from the magazine from the section of the working channel (106) below the magazines (114) into the joining region (104a). The configuration in the joining region (104a) can advantageously be checked via the observation unit (104b). After the desired configuration of implants has been established, the implants are pushed together in the joining region (104a) with the help of the mandrel (107) and joined to form a seed-spacer chain. As an abutment, a first lock (110), which includes a button (110a), blocks during the joining process a transition from the working channel (106) to the needle holder (103). After joining, the first lock (110) is opened, thereby allowing the ejection of joined implant chains via the needle holder (103) into the needle (124) (see FIG. 22). The first lock (110) is thereby preferably arranged in front of the needle holder (103) and behind the observation region (104b), but can also coincide with the needle holder (103).

The manually operable needle holder (103) consists of a locking device and a needle adapter which guides the joined implant chains into the attached needle (124). The locking device of the needle holder holds and secures the needle (124) captive during filling.

A lens-mirror system (109) allows for indirect and thereby radiation-protected visual contact with the implants or chain components. Via a flap (111) in the observation unit (104b), direct access to the working channel (106) is possible, in order to perform possible corrections to the seed-spacer configuration. For short-term, interim storage of the radiation sources or spacers during a correction, two trough-shaped storage places are available below the radiation-protected valve (111).

Both magazines (114) are latchingly fixed during operation of the device (101) via a safety mechanism (123), as shown in FIG. 20, and held captive. The safety mechanism (123) includes a projection engaging in the locking groove (9) of a spacer magazine (118). The magazines (114), however, can be unlocked and removed by operating a corresponding release lever. An swap of magazines (114) in their designated locations is not possible via mechanical encoding. Preferably, the radiation source magazine (116) has encoding different from the encoding of the spacer magazine (118). The encoding can be carried out via an encoding bolt that engages with a corresponding encoding opening (11) of the magazine. The encoding of the radiation source magazine (116) additionally displaces an aforementioned locking slider (5) when the magazine (116) is inserted. This provides additional protection from radiation exposure during handling and during transport of the magazine (116) prior to installation into the device (101). The locking slider (5) closes again after removal of the radiation source magazine (116).

To prevent damage to the implants from excessive force when joining the implants the flange unit (104) is provided with a magnetic coupling (122). The carriage (112) guiding the handle (108) and the mandrel (107) is constructed in two parts, as shown in FIGS. 18 and 19. Both parts separate when the holding force of the magnetic force is exceeded, making further operation of a lever (119) ineffective.

The charging unit (105) includes the slots for a spacer magazine and a radiation source magazine (118, 116) as well as a mechanical lever mechanism (113) for releasing the implants. After inserting a magazine (114) and operating a corresponding button (113a) in the lever mechanism (113), an implant is released from the magazine into the channel (106) below. The lever mechanism (113) for each magazine (114) has a lever mechanism button (113a), preferably slidingly supported, a button rod (113b) with a crosswise groove, whereby the button rod (113b) is preferably a springily supported and beveled one-sided towards the first pressure spring piece (113d). Furthermore, the lever mechanism (113) includes a lever (113c) which is rotatably and springily supported in the housing with a first pressure spring piece (113d) and a push rod (113e) translationally guided transversely to the button rods (113b), with a corresponding second pressure spring piece (113f) for each lever mechanism, as well as a first extension (113g) of the push rod and a second extension (113h) of the push rod.

The lever mechanism (113) will now be described in more detail with reference to FIGS. 18-20. By pressing on the button (113a), the button rod (113b) which is preferably slideably guided on both sides is moved downwards (see FIG. 20), where it presses with its free end onto the springily supported pin of the first pressure spring piece (113d), thereby pressing the pressure spring piece (113d) downward. Because this pressure spring piece (113d) is directly connected to the lever (113c) which is rotationally supported in the housing, button rod (113b) transfers the motion directly to the lever (113c). The lever (113c) thereby lifts the end facing the pressure spring piece (113d), which engages with the magazine disposed above and thereby initiates the release of the implant.

In order to fix the lever mechanism button (113a) in the lower position after actuation, a second pressure spring piece (113f) of the push rod (113e) latches in a crosswise groove of the beveled button rod (113b). Simultaneously, the springy pin of the first pressure spring piece (113d) of the lever (113c) slides along the beveled button rod (113b). Since the lever (113c) is springily supported, it return to its original position. It is the purpose of this mechanism to temporarily secure the button (113a) in the pressed position after actuation, for safety reasons, while allowing the lever (113c) to return to its initial position after activating the magazine (114).

As can be seen in FIGS. 18 and 19, the push rod (113e) is elongated on both sides of the lever mechanism (113), with a first extension (113g) and a second extension (113h). The first extension (113g) of the push rod (113b) is arranged between the magazines (114) and the first lock (110) and can engage in an opening (110b) of the first lock (110) and open the lock button (110a) of the first lock (110). The second extension (113h) of the push rod (113b) is arranged between the magazines and the handle (108) and engages in an opening (119b) of the third lock (119).

If implants (115, 117) were released below the magazine (114) and the buttons (113a) remain in the lower placement, then the handle (108) must first be pushed in the X direction. If the handle is pushed in the X-direction and the third lock (119) is closed, then the user pushes the third lock (119) against the one second extension (113h) with the handle (108) and hence against the push rod (113e). In this state, the second extension (107) is fixed in the opening (119b) of the third lock (119) and is displaced with the handle (108). The second pressure spring pieces (113f) of the push rod (113e) are then pushed out of the crosswise grooves of the button rod (113b), thereby unlocking the buttons (113a). Since movement of the handle (108) also moves the mandrel (107), unlocking the button (113a) automatically displaces the implants from the space below the magazines.

If the third lock (119) is open, then the handle (108) and the mandrel (107) can be displaced in the X-direction without being delimited by the third lock (119) and the second push rod extension (113h). This position is used to join the implant chains and later push them into the needle (123). However, in this position of the third lock (119), the buttons (113a) cannot be unlocked again.

If the first lock (110) was opened to push the implant chain into the needle (123) after joining, the implant chain is fixed in this position to prevent damage to the chain when the lock (110) falls back. It is only closed again by an impulse from the first extension (113g) of the push rod (113e) via the opening (110b), if the carriage with the third lock (119) displaces the second extension (113h). In a closed state, the first lock (110) serves as an abutment for joining the implant chain from the individual implants.

With the lever mechanism (113), ejection of two chain components on top of one another can be prevented. However, the buttons (113a) of the different magazines (114) can also be released simultaneously since they are arranged with a horizontal spacing above the working channel (106). Advantageously, this enables quicker assembly by simultaneous (or within a short time) pressing the buttons (113a) of the radiation source magazine and the spacer magazine.

FIG. 20 shows a cross-section through the device (101) according to the invention at the level of the spacer magazine (118). The handle (108) is visible behind the spacer magazine (118). The safety mechanism (123) of the receiving mechanism for device magazines (101) is located at the level of the spacer magazine (118). The safety mechanism (123) encompasses a projection (123a), arranged, for example, in FIG. 20 at the upper right side, which engages in the locking groove (9) of the spacer magazine (118) and captively holds the magazine (118) in the device (101). The safety mechanism (123) further includes a button (123b) in the upper region. By pushing the button (123b), the projection (123a) of the safety mechanism pivots out of the locking groove (9) and releases the magazine (118). In FIG. 20, the safety mechanism (123) is arranged on one side of the spacer magazine (118), the ejection lever mechanism (113) on the other side. The ejection lever mechanism (113) also includes a button (113a) which is operatively connected with the ejector lever (4) of the magazine (118). By pressing the button (113a) of the lever mechanism (113), the ejector lever (4) is rotated upwards and a spacer (119) is released downwards into the working channel (106). FIG. 21 shows the attached working channel (106) of FIG. 20 in an enlarged view. The working channel (106) preferably has a V-shape, so that the chain components are located and guided at the deepest point of the V.

FIG. 22 shows a needle (124) that is inserted into the needle holder (103) of the device (101). The chain components are pushed by the mandrel (107) out the joining and observation unit and into the needle (124).

In the following, the order of operation of the elements of the device (101) for joining chain components will be briefly summarized:

Actuation of the lever mechanism (113) and ejection of a chain component; blocking of the lever mechanism (113) of the actuated magazine;

Displacement of the handle (108) to move the mandrel (107) along the longitudinal axis of the device in the working channel (106) in order to move the ejected chain component into the joining region and observation region (104a, 104b); release of the previously blocked lever mechanism (113);

Repeating steps 1 and 2 until the required chain components have been released;

Pressing and locking the button (119a) of the third lock (119) on the handle (108) to join the chain components by pressing the chain components with the mandrel (107) against the first lock (110);

Release of the first lock (110) by pressing the button (110a);

Displacing the mandrel (107) to move the joined chain components into a needle (124), Spring-loaded or manual return of the handle (108) to its original position; the first lock (110) is closed again only after renewed displacement of the mandrel (107), preferably by engagement of the first extension (113g) in the first opening (110b) of the first lock (110). In summary, it should be noted that this invention illustrates a fully sterilizable device (101) for the production of radiation source-spacer chains.

The device (101) does not require electromechanical parts. The arrangement of the radiation sources and spacers (115, 117) in the chains can be individually and variably configured commensurate with patient-oriented treatment plan.

For the production of radiation source-spacer chains, the described device (101) only requires two magazines (116, 118), which can minimize confusion during assembly of the chain. The magazines (116, 118) are arranged in a row along the longitudinal axis of the device. This creates a clear and user-friendly overview for the operator.

With the encoding of the device (101) and magazine (116, 118) described above, it becomes impossible to swap the radiation source magazine or spacer magazine during insertion into the device (101).

Both magazines (116, 118) transport the stored implants in a working channel (106) which is arranged below the magazines and open on the top. In this channel (105), the implants are pushed to the front of the device (101), where they will later be joined to a so-called strand. This concept prevents the implants from being moved from the rear magazine (118) through the front magazine (116), which could lead to jamming. Furthermore, this concept prevents damage to the mandrel (107) in the event that a magazine (116, 118) is accidentally removed from the entire construction too early. Ejection of the implants into only a single working channel (106) for removal and joining both chain links minimizes the risk of bending the mandrel (107).

Because of this arrangement of magazines (116, 118) with respect to the working channel (106), it is not necessary to move the magazines (116, 118) at an angle relative to the longitudinal axis of the device to change the implants to be ejected.

The magazines preferably contain more than 50 and up to 100 chain components, which are stored in a space-saving carrousel device. However, more than 100 chain components could also be stored in the magazines. Because of the content of the preferred approx. 100 radiation sources or 100 spacers, most radiation source treatments will only be able to be performed with only one of each of the magazines (116, 118).

Due to the interlocks, the magazine (116, 118) can no longer be released when the radiation source stock or the spacer stock is used up.

The magazines (116, 118) are driven with a constant-force spring (3) which always provides the same force. Blocking of this constant-force spring (3) is produced by an externally-driven anchoring system (4).

The magazines (116, 118) can be reused after treatment. They do not contain any electromechanical parts.

The number of radiation sources and spacers (115, 117) remaining in the magazines can be read at any time on the magazines (116, 118). That obviates the need for counting the spent radiation sources and spacers (115, 117) during and after treatment.

The magazines (116, 118) offer optimal radiation protection because the housing (102) is shielded on all sides. The opening (10) of the radiation source magazine (116) is released only after the magazine (116) containing the active radiation sources (115) has been inserted. After removal of the magazine (116) the opening (10) is closed again. Therefore, radiation protection is ensured for the entire duration of application and during transport, i.e. even outside the device. This functional detail can be omitted for magazines having the non-active spacers (117).

Unlike with prefabricated radiation source-spacer chains, the radiation source-spacer chain configuration which is individually tailored for each patient reduces loose radiation source waste. Unused radiation sources (115) and spacers (117) remain in the corresponding magazines (116, 118). Therefore, radiation exposure cannot occur.

In addition, radiation exposure due to released radiation sources in the working channel (106) is prevented by a shield and an indirect view via a minor.

REFERENCE LIST

1 Magazine
2 Means for receiving chain components or seed repository
3 First tension spring—constant force spring
4 Ejection lever
5 Sliding shutter
6 Depressions
7 Magazine housing
7a Housing cover
7b Housing shell
8 Interior bearing ring
9 Locking groove
10 Ejection
11 Encoding bore
12 Opening
13 Upper sprocket
14 Display
15 Marking
16 Inner wall
17 Central opening
18 Spacer
19 Radiation sources
20 First pressure spring—for ejection lever 4
21 Second pressure spring—for sliding shutter 5
22 Release blocking element in case of empty magazines
101 Assembly device for radiation sources
102 Housing
103 Needle holder
104 Joining area and observation unit
104a Joining area
104b Observation unit
105 Loading unit
106 Working channel
107 Mandrel
108 External handle
109 Mirror-Lens Unit
109a Mirror
109b Lens
110 First lock—Lock in the working channel for assembling chain components
110a First lock button
110b Receiving aperture for the first extension of push rod 113g
111 Flap
112 Carriage
113 Lever mechanism
113a Lever mechanism button
113b Rod of the lever mechanism button
113c Lever
113d First pressure spring piece
113e Push rod
113f Second pressure spring piece
113g First push rod extension
113h Second push rod extension
114 Magazine
115 Radiation source
116 Radiation source magazine
117 Spacer
118 Spacer magazine
119 Third lock—Lock within the handle
119a Third lock button
119b Receiving aperture for the second extension of push rod 113h
120 Installation space for lighting
121 Opening of the loading unit to the working channel
122 Magnetic coupling
123 Magazine safety mechanism
123a Projection for safety mechanism 123
123b Button for safety mechanism 123
124 Needle

What is claimed is:

1. A device for assembling chain components to a chain, wherein at least one chain component comprises radioactive radiation sources, the device comprising:
   a housing,
   a working channel, which extends along a first case axis of the housing,
   a loading unit connected to the working channel and including at least two receiving devices for receiving magazines with chain components, wherein at least one receiving device is configured to receive a radiation source magazine, as well as at least one means for ejecting the chain components from the received magazines, and
   a joining unit for joining chain components,
   characterized in that
   the at least two receiving devices are arranged in such a manner that the magazines for chain components received therein are spaced along the first axis and positioned vertically above the working channel.

2. The device according to claim 1, wherein the second receiving device is configured to receive a spacer magazine with spacers.

3. The device according to claim 1, wherein the joining unit comprises an joining region and an observation unit, so that assembly of the chain can be viewed from the outside.

4. The device according to claim 3, wherein the observation unit is an indirect observation unit, so that the chain can be viewed indirectly and preferably comprises a mirror-lens unit.

5. The device according to claim 1, comprising a flap for opening the housing in the joining region of the joining unit.

6. The device according to claim 1, wherein a needle holder is arranged at one end of the working channel and a first lock is disposed between the needle holder and the joining unit.

7. The device according to claim 1, wherein the joining unit further includes a mandrel, which is constructed for displacement in the working channel along the first axis.

8. The device according to claim 7, wherein the mandrel is constructed to be movably by way of an exterior handle which is movably arranged on the housing.

9. The device according to claim 7, wherein the joining unit further includes a magnetic coupling, so that the exterior handle and the mandrel are separable from each other if a force threshold value is exceeded.

10. The device according to claim 7, wherein the mandrel and the at least one means for ejecting chain components are coupled with one another by a second lock in such a manner that after a one-time actuation of the ejection means, a second actuation of the ejection means is prevented before the mandrel has been displaced.

11. The device according to claim 1, wherein the receiving devices comprise two safety mechanisms for latching, securing and removing magazines with chain components in/from the housing.

12. The device according to claim 1, further comprising a third lock, which in a locked state only enables a mandrel displacement up to a location where assembly of the chain components in the working channel does not yet occur.

13. The device according to claim 12, wherein the third lock is linked with the first lock between the needle holder and the joining unit, so that the first lock can in the needle holder only be unlocked when the third lock is released.

14. The device according to claim 1, wherein the receiving devices comprise elements for encoding, which are configured to cooperate with the corresponding encoding elements of a magazine such that a receiving device is only usable for a special type of magazine.

15. A system for assembling chain components to form a chain with radioactive radiation sources, comprising:
a housing,
a working channel which extends along a first axis of the housing,
a loading unit connected with the working channel and comprising at least two receiving devices for receiving magazines having chain components and at least one means for ejecting the chain components from the received magazines,
a first magazine for radioactive radiation sources, arranged in one of the at least two receiving devices,
a second magazine for additional chain components different from the radiation sources, arranged in the other of the at least two receiving devices,
a joining unit for joining the chain components,
characterized in that
the working channel does not pass through the magazines, and
the first magazine for radioactive radiation sources and the second magazine for additional chain components are spaced along the first axis and vertically positioned above the working channel so that the chain components are ejected downwards into the working channel.

* * * * *